(12) United States Patent
Dye et al.

(10) Patent No.: US 6,395,004 B1
(45) Date of Patent: May 28, 2002

(54) ORTHOPEDIC TRIAL PROSTHESIS AND SAW GUIDE INSTRUMENT

(75) Inventors: Donald W. Dye, Plugerville; Stephen W. Haecker; Adriana de la Barcena, both of Austin, all of TX (US)

(73) Assignee: Sulzer Orthopedics Inc., Austin, TX (US)

( * ) Notice: Subject to any disclaimer, the term of this patent is extended or adjusted under 35 U.S.C. 154(b) by 0 days.

(21) Appl. No.: 08/970,650

(22) Filed: Nov. 14, 1997

(51) Int. Cl.$^7$ ................................................ A61B 17/56
(52) U.S. Cl. ........................................................ 606/86
(58) Field of Search ............................... 623/16, 18, 22, 623/23; 606/86, 89, 87

(56) References Cited

U.S. PATENT DOCUMENTS

| | | | | |
|---|---|---|---|---|
| 3,814,089 A | * | 6/1974 | Deyerle | 606/89 |
| 4,911,722 A | * | 3/1990 | Crespy | 623/23 |
| 4,936,863 A | * | 6/1990 | Hofmann | 623/23 |
| 4,959,066 A | | 9/1990 | Dunn et al. | |
| 5,070,623 A | | 12/1991 | Barnes | |
| 5,108,396 A | | 4/1992 | Lackey et al. | |
| 5,211,666 A | * | 5/1993 | Fetto | 623/23 |
| 5,246,461 A | * | 9/1993 | Tepic | 623/23 |

OTHER PUBLICATIONS

Dunn, Harrold K., M.D. Surgical Technique for Primary Hip.
Arthoplasty Advancing The Science of Implant Stability, p. 10.

* cited by examiner

Primary Examiner—David J. Isabella
(74) Attorney, Agent, or Firm—Philip S. Lyren

(57) ABSTRACT

A trial prosthesis and saw guide system for use in orthopedic surgery to implant an orthopedic calcar-replacing femoral hip prosthesis. A trial femoral hip stem includes a longitudinal axis, a proximal portion and a distal portion, and a neck portion for temporarily receiving a trial femoral head. The proximal portion includes an elongate saw guide slot substantially parallel to the longitudinal axis. A trial femoral hip flange is provided for temporary insertion within the saw guide slot. An elongate rotary reamer is provided for reaming a socket in the medullary canal to receive the hip prosthesis. An elongate driver adapter has means at a proximal end for connection to a powered rotary driver and has means at a distal end for connection to the elongate rotary reamer. An osteotomy guide has means for connection to the elongate driver adapter for rotary motion about the axis of the driver adapter, and includes a saw guide having a saw capture slot for capturing a saw blade to control the plane of cutting of the saw blade. The saw capture slot is oriented substantially perpendicular to the axis of the elongate driver adapter. Markings are provided on the osteotomy guide that align with the proximal extent of the greater trochanter to indicate that the saw guide slot is disposed in the proper plane. Means are provided on the osteotomy guide and driver adapter for controlling the axial position of the osteotomy guide relative to the driver adapter.

6 Claims, 4 Drawing Sheets

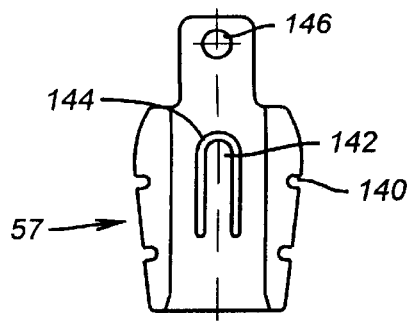
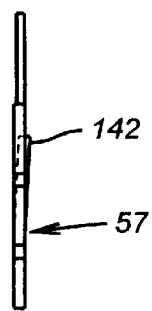
FIG. 12  FIG. 11
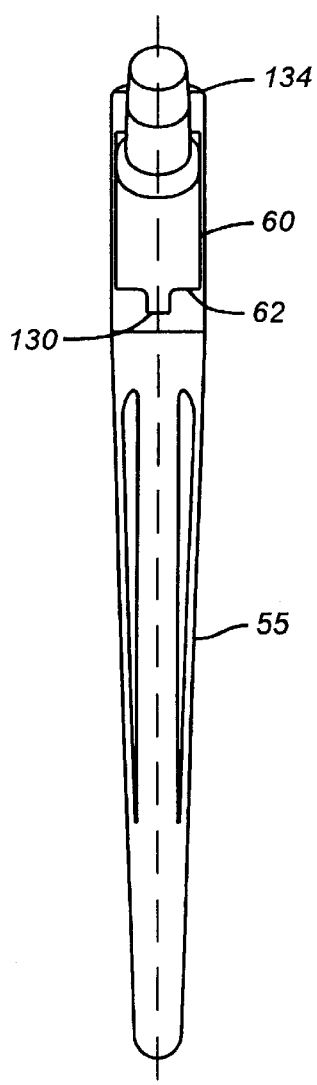
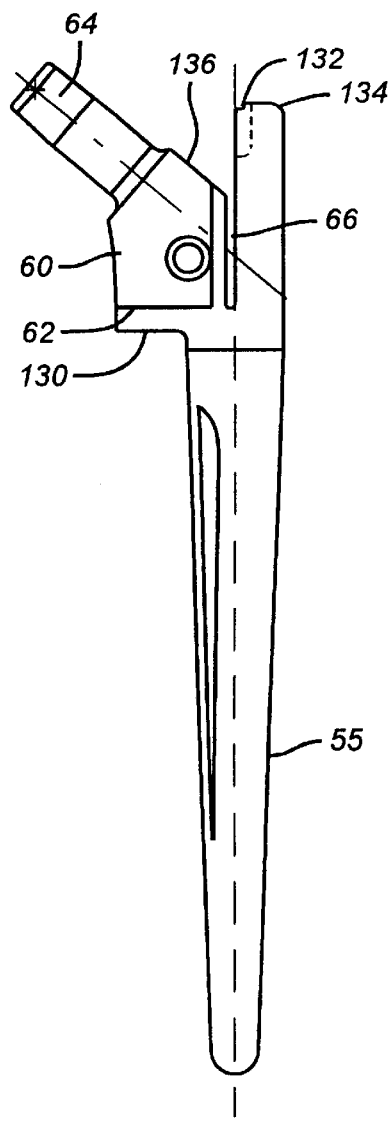
FIG. 10  FIG. 9

ORTHOPEDIC TRIAL PROSTHESIS AND SAW GUIDE INSTRUMENT

BACKGROUND OF THE INVENTION

1. Field of the Invention

This invention relates generally to implantable orthopedic prostheses and more particularly to instruments and surgical techniques for implanting orthopedic prostheses.

2. Background Art

Implantable orthopedic prostheses, in their most common form, comprise man-made replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the hip joint and the knee joint are the ones most often treated with such prostheses. One reason for this is that the hip and knee joints are major weight bearing joints and degenerate more quickly than other joints in the event of abnormality. Another reason is that the hip and knee joints play a critical role in ambulation and quality of life, resulting in a greater demand for surgical correction of abnormalities.

With particular regard to the hip joint, the commonly employed orthopedic prostheses include components that fall within one of three principle categories: femoral stems, femoral heads and acetabular cups. A so-called "total" hip prosthesis includes components from each of those categories. The femoral stem replaces the proximal end of the femur and includes a distal stem that is received within the medullary canal at the proximal end of the femur. The femoral head replaces the natural head and articulating surface of the femur. The acetabular cup replaces the natural socket and articulating surface of the acetabulum of the pelvis. In some designs, the stem and head are an integral, unitary component, but more often the stem and head are separate modular components designed to be assembled together to suit the anatomical needs of the patient. In some other designs, including the so-called "bipolar" hip prostheses, only the femoral part of the hip joint is replaced and the artificial femoral head articulates directly against the natural acetabulum. In the case of the bipolar hip prosthesis, there is a second inner head that articulates within the outer head, hence the origin of the term "bipolar."

Considering specifically the femoral stem component of implantable orthopedic prostheses, various configurations are available for use. The configuration that is most appropriate for a particular patient is often dictated by the condition of the bone of the proximal femur at the time the surgery is contemplated. Considered broadly, hip stems can be classified as either primary or revision stems, although some designs admit of use in either class. In general, primary hip stems are used for the first implantation in a particular femur, as they are the most bone-conserving by design. Likewise, the design of the primary stem is based on the assumption that the bone of the proximal femur is generally sound, except for the neck and the articulating surface of the head. Consequently, a primary stem may not be suitable where structurally critical bone of the proximal femur is unsound, or missing. Revision stems are designed for use in second and subsequent implantations in a particular femur, where there has been some loss of bone from prior surgery or from failure of a prior implant. In some patients, a revision stem would be the stem of choice for a first implantation where the bone of the proximal femur is unusually compromised.

One hip stem design, known as the calcar-replacing hip stem, typically employed as a revision stem, is particularly suited for use where the calcar femorale, a bony spur springing from the underside of the neck of the femur above and anterior to the lesser trochanter, is missing or compromised. The calcar femorale is important in providing structural strength to the proximal femur, and its absence contraindicates the use of a conventional primary or revision stem that depends on the calcar for support. The calcar-replacing hip stem includes a substantially horizontal flange designed to engage a horizontal proximal surface of the proximal femur that is created by resecting the femur below the natural location of the calcar femorale. Typically, the proximal femur is resected by two orthogonal planar osteotomies, one that is horizontal and extends from the medial side of the femur to about half-way to the lateral side, and one that is vertical and extends from the proximal extent of the femur down to the horizontal osteotomy. Consequently, a right-angular quadrant of the femur, including the neck and head, is resected. The calcar-replacing hip stem also includes a substantially vertical flange that engages the vertical resected surface of the proximal femur.

The current state of the art of fitting a calcar-replacing femoral stem prosthesis to a femur involves performing the horizontal and vertical osteotomies with a powered reciprocating saw blade, but in a freehand manner that depends for its success on the skill and technique of the implanting surgeon in making those osteotomies at the correct locations and in the proper planes. Any error in performing the osteotomies can result in the flanges of the calcar-replacing prosthesis not engaging the resected bony surfaces properly, or in the prosthesis being placed too low or too proud, or too lateral or too medial, with a consequent failure to restore the natural anatomic dimensions of the femur. It is desirable that the medullary canal be reamed to create a bony socket that closely conforms to the contour of the distal stem of the prosthesis. Ideally, when the prosthesis is inserted into the reamed medullary canal, the horizontal flange should engage the transversely resected horizontal bony surface approximately simultaneously with the distal stem becoming seated in engagement with the bony socket. Unless the relationship between the depth of the reamed socket and the location of the horizontal osteotomy is well-controlled, that ideal simultaneous engagement may not be achieved, resulting in the prosthesis-to-bone fit being less than optimum overall.

It would be desirable to provide an instrument system that provides for precise control and repeatability of the various reaming and osteotomy steps involved in implanting a calcar-replacing hip stem prosthesis to improve the ultimate fit of the prosthesis to the femur and to improve the outcome for the patient. Such desirable ends are achieved by the present invention, a preferred embodiment of which is described herein.

SUMMARY OF THE INVENTION

According to one aspect of the present invention, a trial prosthesis and saw guide instrument system is provided for use in orthopedic surgery to implant an orthopedic calcar-replacing femoral hip prosthesis. The instrument system comprises a trial femoral hip stem and trial flange, for temporary insertion at a resected proximal end of a femur within a reamed intramedulary canal of the femur. The trial femoral hip stem includes a longitudinal axis, a proximal portion and a distal portion, and a neck portion for temporarily receiving a trial femoral head. The proximal portion includes an elongate saw guide slot, substantially parallel to the longitudinal axis. The trial flange is configured for temporary insertion within the saw guide slot to simulate a vertical flange of a calcar-replacing femoral hip stem prosthesis.

According to another aspect of the present invention, an osteotomy guide and saw guide instrument system is provided for use in orthopedic surgery to implant an orthopedic calcar-replacing femoral hip prosthesis. The instrument system includes an elongate rotary reamer for reaming a socket in the medullary canal to receive the hip prosthesis, and an elongate driver adapter configured at a proximal end thereof for connection to a powered rotary driver and configured at a distal end thereof for connection to the elongate rotary reamer. An osteotomy guide has means for connection to the elongate driver adapter for rotary motion about the axis of the driver adapter, and includes a saw guide having a saw capture slot for capturing a saw blade therein to control the plane of cutting of the saw blade. The saw capture slot is oriented substantially perpendicular to the axis of the elongate driver adapter. Markings on the osteotomy guide, when aligned with the proximal extent of the greater trochanter, provide indication that the saw guide slot is disposed in the proper plane for guiding the transverse osteotomy. Means are provided on the osteotomy guide and driver adapter for controlling the axial position of the osteotomy guide relative to the driver adapter.

According to another aspect of the present invention, an osteotomy guide and saw guide instrument system is provided for use in orthopedic surgery to implant an orthopedic calcar-replacing femoral hip prosthesis. The instrument system includes a trial femoral hip stem for temporary insertion at a resected proximal end of a femur within a reamed intramedullary canal of the femur, and an elongate rotary reamer for reaming a socket in the medullary canal to receive the hip prosthesis. An elongate driver adapter has a proximal end configured for connection to a powered rotary driver and has a distal end configured for connection to the elongate rotary reamer. An osteotomy guide has means for connection to the elongate driver adapter for rotary motion about the axis of the driver adapter, and includes a saw guide surface for guiding a saw blade to control the plane of cutting of the saw blade. The saw guide surface is disposed in a plane substantially parallel to the axis of the elongate driver adapter and is offset medially from the axis by a distance sufficiently medial to prevent contact between the saw blade and the means for connection, and sufficiently lateral to guide a vertical osteotomy at a location where the spacing in the anterior-posterior direction between the inner cortical bone surfaces exceeds the spacing necessary to allow passage of the trial femoral hip stem therebetween.

It is an object of the present invention to provide surgical instrumentation that enables precise control and repeatability of various reaming and osteotomy steps involved in implanting a calcar-replacing hip stem prosthesis. Other objects and advantages of the present invention will be apparent from the following detailed description of a preferred embodiment, made with reference to the drawings.

BRIEF DESCRIPTION OF THE DRAWINGS

FIG. 9 is a front elevational view of a trial prosthesis component of the instrument system of FIG. 1.

FIG. 10 is a side elevational view of the trial prosthesis component of FIG. 9.

FIG. 11 is a front elevational view of a modular flange for use with the trial prosthesis component of FIG. 9.

FIG. 12 is a side elevational view of the modular flange of FIG. 11.

DETAILED DESCRIPTION OF THE PREFERRED EMBODIMENT

Figure 1:
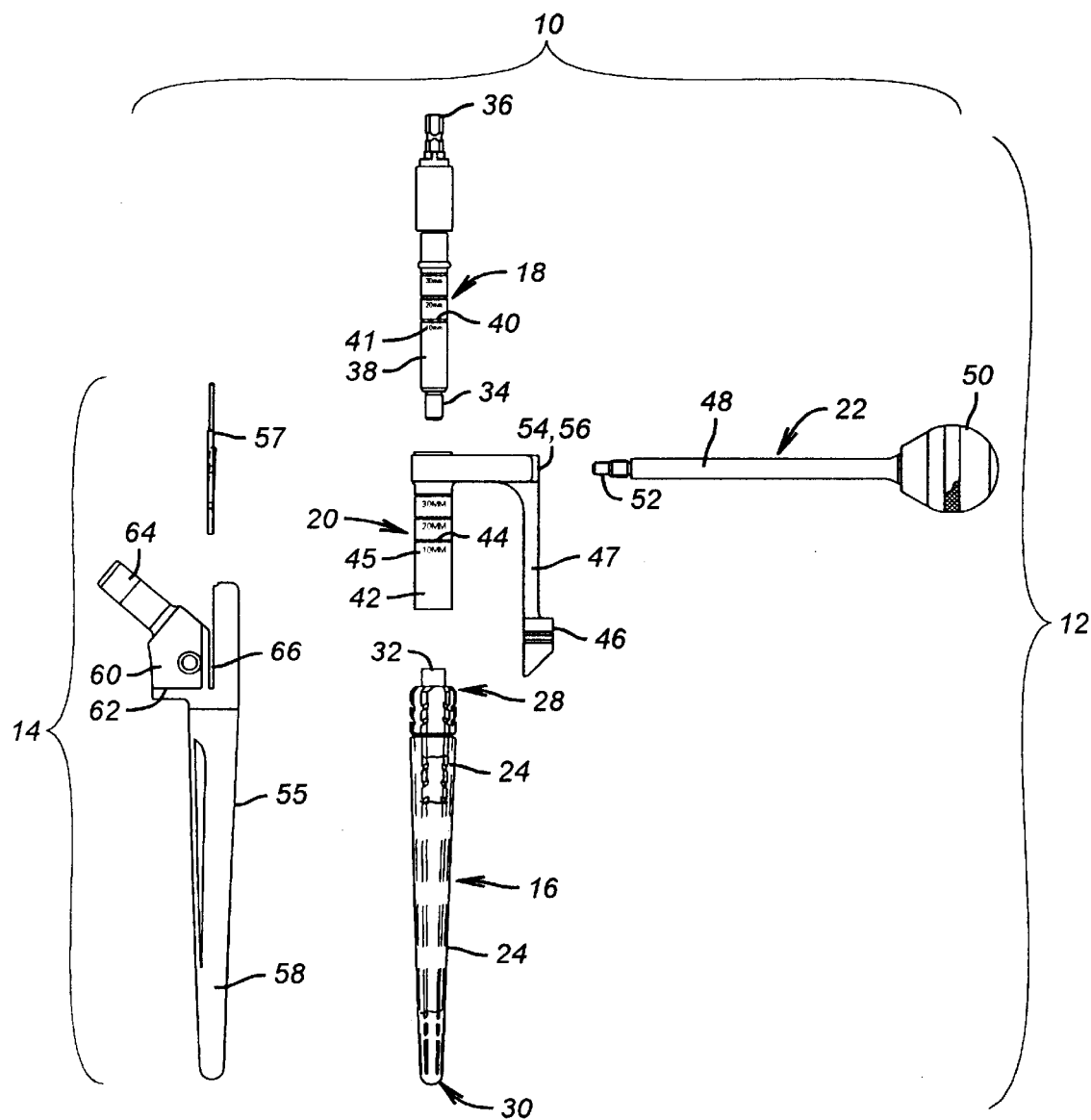
FIG. 1 is an exploded elevational view of an instrument system configured in accordance with the present invention, particularly illustrating subsystems of components of the instrument system.

Referring to FIG. 1, there is illustrated a preferred embodiment of an instrument system 10 incorporating the present invention. The instrument system 10 is particularly useful in connection with the surgical implantation of a femoral hip stem prosthesis of the calcar-replacement type. The surgical technique for implanting calcar-replacement type hip stem prostheses typically requires a transverse, i.e., substantially horizontal, first osteotomy to resect the proximal end of the femur partially therethrough to establish a bony surface for abutment with a horizontal flange of the prostheses. A subsequent longitudinal, i.e., substantially vertical, second osteotomy, intersecting the first osteotomy at substantially a right angle, is required to resect the proximal end of the femur to establish a bony surface for abutting a lateral surface of a vertical flange of the prosthesis. The surgical technique also requires reaming the medullary canal of the proximal femur to create a bony socket for receiving an elongate distal stem of the femoral hip stem prosthesis. Instrument system 10 comprises two primary subsystems for facilitating the surgical operations just mentioned: an osteotomy guide, reamer, and driver adapter subsystem 12, and a trial prosthesis and trial flange subsystem 14.

Still referring to FIG. 1, and with particular reference to subsystem 12, the reamer 16, driver adapter 18, osteotomy guide 20, and handle 22 are described generally below, with respect to their interconnection and use.

Reamer 16, having an outer surface 24 comprising cutting teeth 26, tapers from its proximal end 28 to its distal end 30. Surface 24 has a configuration that results in the medullary canal having a reamed cross-section that generally conforms along its length to the corresponding cross-section of the calcar-replacement prosthesis that is to be implanted. The proximal end 28 of reamer 16 has a threaded blind hole 32 disposed coaxially with the longitudinal axis of reamer 16, and open at the proximal end thereof. Removably connected to reamer 16 is driver adapter 18, having a correspondingly threaded male distal end 34 that is threadedly receivable in threaded hole 32. The proximal end 36 of driver adapter 18 is configured to mate with a selected power instrument for providing rotary drive power. Driver adapter 18 includes a shaft 38 intermediate the proximal and distal ends 36 and 34, which shaft 38 is inscribed with markings 40 at regular intervals, identified with appropriate indicia 41. The markings are useful to the surgeon during the reaming operation to indicate the depth to which the medullary canal has been reamed. More particularly, the surgeon terminates reaming when the depth marking 40, corresponding to the recommended depth for the prosthesis that has been selected for implanting, becomes aligned with the proximal tip of the greater trochanter of the femur.

Osteotomy guide 20 includes a tubular portion 42 configured to be received over shaft 38 of driver adapter 18 in sliding and rotating relationship. When so received, osteotomy guide 20 can be captured for sliding between reamer 16 and proximal end 34 of driver adapter 20. Such capture is effected by attaching threaded end 34 of driver adapter 18 to threaded hole 32 in reamer 16. Tubular portion 42 is inscribed with markings 44 at regular intervals, identified with appropriate indicia 45. The markings 44 correspond in placement and purpose to the markings 40 described above on the driver adapter 18, and are similarly useful to the surgeon. More specifically, the osteotomy guide 20 is used with the reamer 16 to control the depth of the reaming of the medullary canal. The surgeon terminates reaming when the depth marking 45 on the tubular portion 42, which overlies the similar depth marking 41 on the driver adapter at the same relative position, becomes aligned with the proximal tip of the greater trochanter of the femur. At that point, with the reamer 16 disposed at the ultimate depth, a saw capture slot 46 of the osteotomy guide 20 stands disposed at the appropriate point along the length of the femur to ensure that an osteotomy saw blade captured in slot 46 can perform the horizontal osteotomy at the correct location and in the proper plane. The osteotomy so performed results in a resected bone surface that will abut the horizontal flange of a calcar-replacement hip stem prosthesis that is implanted with the distal stem fully seated in the reamed medullary canal. A further function of osteotomy guide 20 is to provide a vertical guide surface 47 against which the osteotomy saw blade is braced while performing an initial rough cut of the vertical osteotomy. The final cut of the vertical osteotomy is subsequently guided more precisely by the other subsystem of the instrument system, described below.

Handle 22, having a shaft 48 and ball grip 50, includes an externally-threaded end 52 that is threadedly received in one of two internally-threaded holes 54 and 56 of osteotomy guide 20, for the purpose of setting the anteversion of saw guide slot 46 prior to performing the transverse horizontal and rough vertical osteotomies.

Again referring to FIG. 1, and with particular reference to subsystem 14, trial prosthesis 55 and trial flange 57 are described generally below, with respect to their interconnection and use. Trial prosthesis 55 is in many respects substantially similar in configuration to the implantable calcar-replacing hip stem prosthesis which is to be implanted. Trial prosthesis 55, and its associated trial flange 57, serve both as a precision saw guide for the final vertical osteotomy, and as a trial prosthesis to gauge the quality of the bone preparation prior to inserting the permanent implantable calcar-replacing prosthesis. Trial prostheses 55 includes a distal stem portion 58 and a proximal body portion 60, the latter including a horizontal flange 62 corresponding to the horizontal flange of the implantable prosthesis. A tapered neck 64 for receiving a trial head prosthesis is provided to allow the surgeon to verify the range of motion of the joint prior to implanting the permanent prosthesis. A vertical slot 66 in the proximal body 60 of trial prosthesis 54 receives a modular trial flange 57 therein, which trial flange 57 duplicates the vertical flange of the implantable prosthesis when fully seated within slot 66. With trial flange 57 removed, slot 66 serves as a saw guide capture slot to receive and guide a reciprocating osteotomy saw blade, thereby providing precision guidance to the location, plane and extent of the vertical osteotomy. More specifically, after the medullary canal has been reamed to the proper depth with the aid of the osteotomy guide 20, and the horizontal and first rough vertical osteotomies have been performed with the aid of the osteotomy guide 20, the reamer 16 and osteotomy guide 20 are removed from the femur and the trial prosthesis 55 is inserted in the prepared medullary canal. Abutment of the horizontal flange 62 of the trial prosthesis against the transversely resected surface of the bone confirms that the implantable prosthesis will fit properly when inserted. Leaving the trial prosthesis in place in the prepared canal, the final vertical osteotomy is performed using the slot 66 as a saw-capturing saw guide. Thereafter, the saw blade is withdrawn and the trial flange 57 is inserted into slot 66, with the trial prosthesis 55 remaining in the prepared medullary canal. Provided that flange 57 can be made to seat fully in slot 66, a positive indication is provided that no bony obstructions remain that would interfere with the vertical flange of the implantable prosthesis. By providing the vertical flange of the trial prosthesis as a separate modular element, rather than an integral part of the trial prosthesis, one can be assured that the stem portion 58 of trial prosthesis 55 is fully seated in the medullary canal. In contrast, a vertical flange that is integral with the trial prosthesis conceivably could hang up on some bony obstruction during insertion of the trial prosthesis, thereby preventing the stem 58 from being fully seated in the prepared medullary canal, with that failure to seat escaping detection.

Each of the components of subsystems 12 and 14 are described in greater detail below, with reference to FIGS. 2–12.

Figure 2:
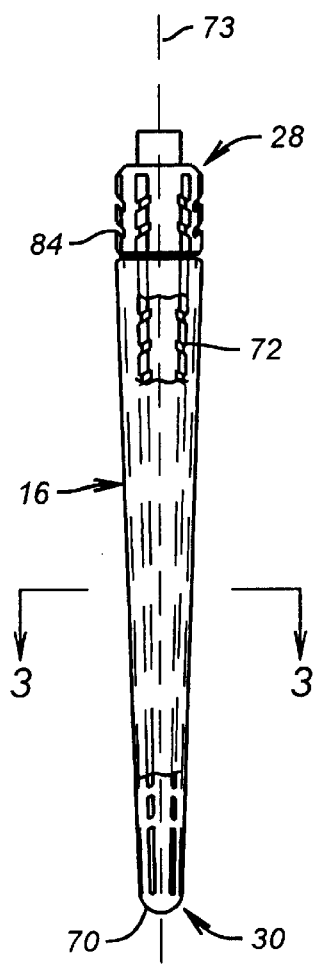
FIG. 2 is an elevational view of a reamer component of the instrument system of FIG. 1.
Figure 3:
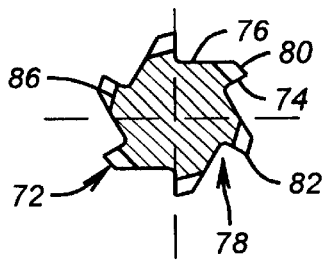
FIG. 3 is a cross-sectional view of the reamer component of FIG. 2, taken along section plane 3—3 of FIG. 2 and viewed in the direction of the arrows.
Figure 8:
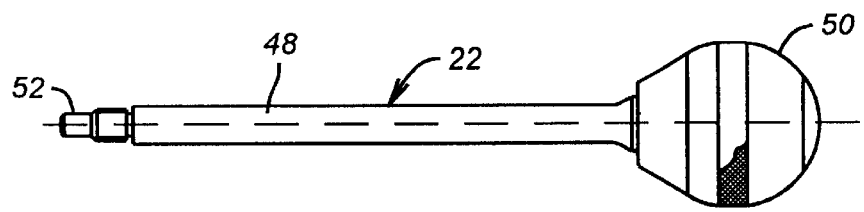
FIG. 8 is an elevational view of a handle for the osteotomy saw guide component of FIG. 5.

With particular reference to FIGS. 2 and 3, reamer component 16 is shown to have a generally conical profile along substantially the entire length thereof from proximal end 28 to distal end 30, which terminates with a blunt, hemispherical surface 70. A plurality, preferably six, longitudinal ribs 72 extend generally radially from reamer 16 and along the length thereof from proximal end 28 to distal end 30 parallel to the central axis 73 of reamer 16. Each rib 72 is particularly configured for efficient cutting of bone when reamer 16 is rotated in a selected direction of rotation, i.e., clockwise when viewed axially from the proximal end 28, as shown in FIG. 3. A leading surface 74 of each rib 72 extends generally radially from axis 73, but is slightly undercut. A trailing surface 76 of each rib 72 extends substantially perpendicular to the radius that defines the leading surface of the preceding (in direction of cutting) rib 72, and intersects the leading surface 74 of that preceding rib 72 to define a flute 78. An outer surface 80 of each rib 72 connects leading and trailing surfaces, 74 and 76, respectively. The intersection of leading surface 74 and outer surface 80 defines a cutting edge 82. Outer surface 80 recedes radially inwardly from edge 82 at a slight angle, such that edge 80 comprises the radially outermost extent of rib 72. The edges 82 of the ribs 72 collectively define the conical profile of reamer 16. The outer surface 80, and consequently the edge 82, is interrupted at periodic intervals by transverse chip breaking grooves 84, each groove having a bottom wall 86 that is substantially parallel to outer surface 82. The depth of each groove 84 is less than the depth of the flutes 78. Grooves 84 are each disposed at an angle of about 60° relative to axis 73. As preferred, all of the grooves 84 of each rib 72 are oriented in the same direction of slope, whereas the direction of slope of the grooves 84 alternates from each rib 72 to the next following rib 72.

Figure 4:
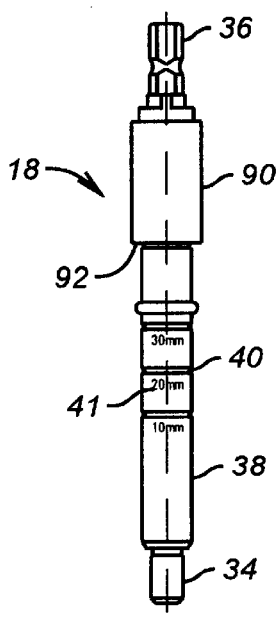
FIG. 4 is an elevational view of a driver adapter component of the instrument system of FIG. 1.

Referring to FIG. 4, driver adapter 18 is illustrated in greater detail. The threaded distal end 34, proximal tool-engaging end 36, shaft 38, markings 40, and indicia 41 were described generally above. As preferred, markings 40 comprise annular, round-bottomed grooves. A portion 90 of shaft 38, intermediate tool-engaging end 36 and that portion of shaft 38 that carries markings 40, is of enlarged diameter to define an annular shoulder 92. As described generally above, shoulder 92 captures tubular portion 42 of the osteotomy guide, described more fully below.

Figure 5:
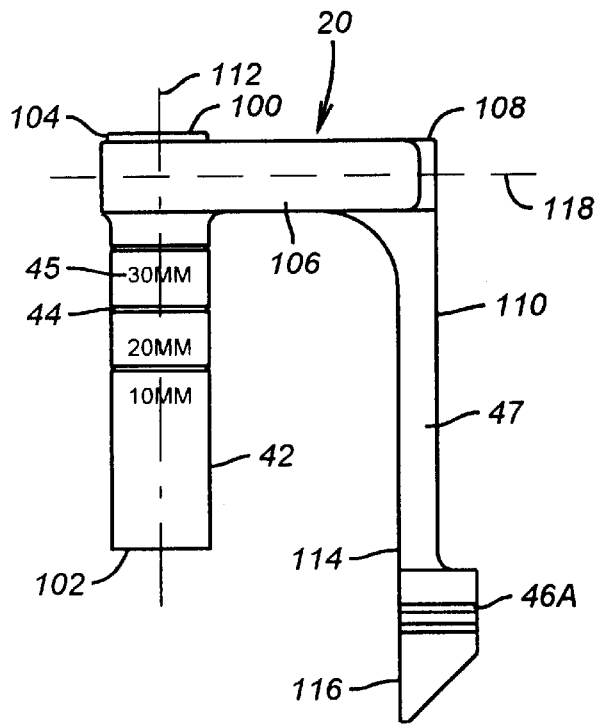
FIG. 5 is a side elevational view of an osteotomy saw guide component of the instrument system of FIG. 1.
Figure 6:
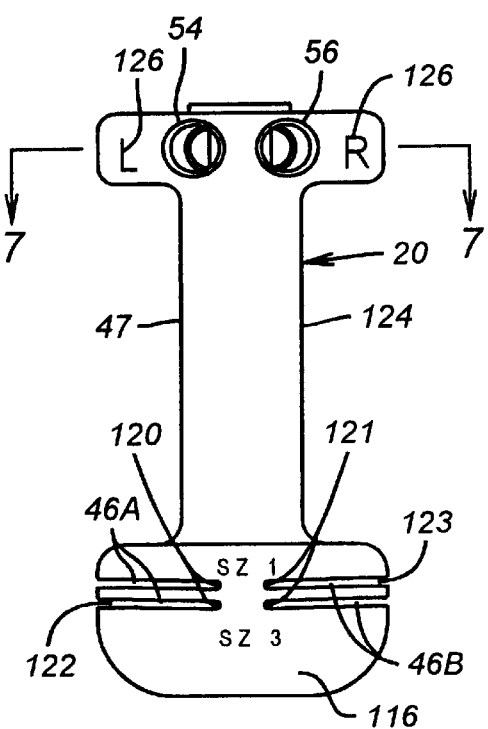
FIG. 6 is a front elevational view of the osteotomy saw guide component of FIG. 5.
Figure 7:
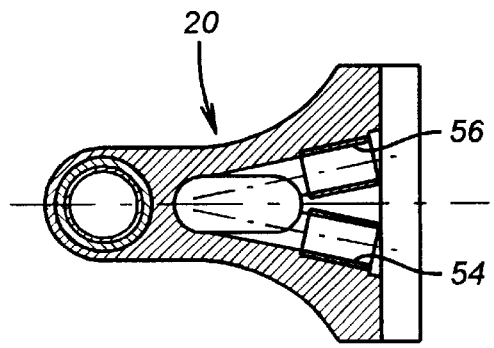
FIG. 7 is a cross-sectional view of the osteotomy saw guide component of FIG. 5, taken along section plane 7—7 of FIG. 6 and viewed in the direction of the arrows.

Referring to FIGS. 5 and 6, osteotomy guide 20, described generally above, is shown in greater detail. Hollow tubular portion 42, fitted internally with poly(amide)imide (DuPont® Vespel®) bushings to provide rotating and sliding bearing support relative to shaft 38 of driver adapter 18, includes an annular proximal end 100, and an annular distal end 102. The internal bushing proximate to annular end 100 includes a radially-extending flange 104 that overlies proximal end 100 to form an annular thrust bearing for engaging shoulder 92 of enlarged portion 90 of driver adapter 18. Extending radially from proximal end 100 of tubular portion 42 is a radial arm 106. Depending from the outermost end 108 of arm 106 is saw guide support arm 110, which extends generally parallel to the axis 112 of tubular portion 42. At the distal end 114 of saw guide support arm 110 is saw guide 116, comprising an elongate block oriented generally transverse to the axis 112 of tubular portion 42, and substantially perpendicular to the radius 118 along which radial arm 106 extends. Saw guide 116 includes a plurality of saw capture slots 46A, described generally above, and a plurality of saw capture slots 46B. Each slot 46A is disposed in a plane that is generally perpendicular to axis 112 of tubular portion 42, with the exception that in the direction perpendicular to both axis 112 and radius 118, the plane of each slot 46A is disposed to slope slightly proximally from the innermost closed end 120 to the outermost open end 122. Similarly, each slot 46B is disposed in a plane that is generally perpendicular to axis 112 of tubular portion 42, with the exception that in the direction perpendicular to both axis 112 and radius 118, the plane of each slot 46B is disposed to slope slightly proximally from the innermost closed end 121 to the outermost open end 123. Saw guide 116 is of sufficient thickness in the direction parallel to radius 118 that saw capture slots 46A and 46B provide control of the plane of orientation of the saw blade captured therein, i.e., the captured saw blade is not free to pivot about an axis transverse to axis 112. As described generally above, saw guide support arm 110 includes a side surface offset transversely from the plane defined by axis 112 and radius 118 to function as a saw guide surface 47. A saw blade, the broad surface of which is held flush against saw guide surface 47, will be disposed in the proper plane to make the rough vertical osteotomy on the right femur. The opposite side surface 124 of saw guide support arm 110 functions similarly to saw guide surface 47 when osteotomy guide 20 is used on the left femur. The plane of saw guide surfaces 47 and 124, respectively, is offset medially relative to axis 112. The amount of offset is selected to meet two criteria. The first criteria is that the offset be sufficient that the saw blade will not strike tubular portion 44, i.e. the amount of offset exceeds the radius dimension of tubular portion 44. The second criteria is that the amount of medial offset be restricted sufficiently that the rough vertical cut is placed at a location where the spacing between the inner cortical surfaces of the femur, in the anterior-posterior direction, is sufficiently great to permit the trial stem 54 to be inserted into the reamed medullary canal without obstruction by cortical bone. Threaded holes 54 and 56, described generally above, are oriented perpendicular to axis 112, but at an angle of about 12° relative to radius 118. Handle 22, shown in detail in FIG. 8, whose threaded end 52 is received in either hole 54 or 56, depending on whether osteotomy guide 20 is being used on the left or right femur, respectively, provides a location for the surgeon to grasp to control the rotational position of osteotomy guide 20 about axis 112. Left and right indicia 126 provide a positive reminder to the surgeon as to which hole, 54 or 56, to use with the left and right femur, respectively. With the knee joint of the femur of interest in flexion, proper angular orientation of the osteotomy guide relative to the femur is obtained by aligning the shaft 48 of handle 22 parallel to the tibia, with handle 22 disposed posteriorly of the femur.

Referring to FIGS. 9 and 10, trial prosthesis 55 is shown in greater detail. In addition to the features and characteristics described generally above, trial prosthesis 55 includes a rib 130 that extends in the medial-lateral direction, and extends distally from horizontal flange 62. During implantation, the surgeon cuts a notch in the cortical bone at the medial aspect to receive rib 130. The engagement of rib 130 and the bone notch provides additional stability of the prosthesis against rotation. A recess 132 located at the proximal end 134 of trial prosthesis 55 opens proximally and medially, and is immediately adjacent the plane of vertical slot 66. Recess 132 provides an access port into which an instrument can be inserted to grasp and remove trial flange 57 from slot 66. Slot 66 terminates well below the proximal end 134 of trial prosthesis 55, at its intersection with medial-proximal surface 136. The space located between medial-proximal surface 136 and proximal end 134 provides clearance to avoid impingement of trial stem 55 and the acetabular prosthesis during a trial reduction of the hip joint during surgery.

Referring to FIGS. 11 and 12, trial flange 57, described above, is shown in greater detail. Trial flange 57 is substantially a flat plate having a thickness at a central portion selected to fit snugly within slot 66, and having a perimetrical contour conforming to that of the vertical flange of the corresponding implantable prosthesis. The thickness of trial flange 57 at locations that extend beyond the proximal body 60 of trial prosthesis 55 in the anterior and posterior directions corresponds to that of the vertical flange of the implantable prosthesis. A plurality of notches 140 on the anterior and posterior edges of trial flange 57 correspond to the suture notches on the vertical flange of the implantable prosthesis. A tongue 142, formed by a U-shaped through slot 144, is canted slightly out of plane from the trial flange 57 to form a cantilever spring that retains trial flange 57 securely, but removably, within vertical slot 66. A through-hole 146 near the proximal end of trial flange 57 is provided for receipt of the removal instrument discussed above with respect to recess 132.

The present invention has been described with particularity in terms of a preferred embodiment, by way of illustration and not limitation. The scope of the invention is defined by the claims appended hereto. Variations of the particular embodiments described herein that incorporate the principles of the present invention may still fall within the scope of the appended claims.

We claim:

1. A trial prosthesis and saw guide system, for use in orthopedic surgery to implant an orthopedic calcar-replacing femoral hip prosthesis, comprising:
   a trial femoral hip stem, for temporary insertion at a resected proximal end of a femur within a reamed intramedullary canal of said femur, said trial femoral hip stem including:
      a longitudinal axis,
      a proximal portion and a distal portion, and
      a neck portion, for temporarily receiving a trial femoral head, extending medially and proximally from said proximal portion at an acute angle relative to said longitudinal axis,
      said proximal portion including an elongate saw guide slot, substantially parallel to said longitudinal axis, extending through said proximal portion anteriorly and posteriorly,
      said proximal portion including a lateral section disposed laterally of said saw guide slot and a medial section disposed medially of said saw guide slot, said lateral section extending proximally beyond said medial section; and
   a trial femoral hip flange, for temporary insertion within said saw guide slot, dimensioned such that, when fully seated distally within said saw guide slot, a proximal end of said flange is substantially aligned with the proximal extent of said lateral section.

2. The trial prosthesis and saw guide system of claim 1, in which said trial femoral hip stem includes a bone-engaging flange substantially perpendicular to said longitudinal axis.

3. The trial prosthesis and saw guide system of claim 2, in which said trial femoral hip stem includes a rib extending distally from said bone engaging flange.

4. The trial prosthesis and saw guide system of claim 1, in which said trial femoral hip flange includes a canted spring tongue for engaging said saw guide slot to retain said trial femoral hip flange within said saw guide slot.

5. The trial prosthesis and saw guide system of claim 4, in which said trial femoral hip stem includes a bone-engaging flange substantially perpendicular to said longitudinal axis.

6. The trial prosthesis and saw guide system of claim 5, in which said trial femoral hip stem includes a rib extending distally from said bone engaging flange.

* * * * *